United States Patent
Bischoff

(10) Patent No.: US 12,042,020 B2
(45) Date of Patent: Jul. 23, 2024

(54) METHOD FOR DETERMINING CHARACTERISTIC FOOT DATA, COMPUTER PROGRAM AND APPARATUS

(71) Applicant: Martin Bischoff, Ansbach (DE)

(72) Inventor: Martin Bischoff, Ansbach (DE)

( * ) Notice: Subject to any disclaimer, the term of this patent is extended or adjusted under 35 U.S.C. 154(b) by 935 days.

(21) Appl. No.: 16/971,327

(22) PCT Filed: Nov. 28, 2018

(86) PCT No.: PCT/EP2018/082758
§ 371 (c)(1),
(2) Date: Aug. 20, 2020

(87) PCT Pub. No.: WO2019/161952
PCT Pub. Date: Aug. 29, 2019

(65) Prior Publication Data
US 2021/0085034 A1    Mar. 25, 2021

(30) Foreign Application Priority Data

Feb. 20, 2018   (DE) ..................... 10 2018 103 695.7

(51) Int. Cl.
*A43D 1/00*    (2006.01)
*A43D 1/02*    (2006.01)
*A43D 1/08*    (2006.01)
*A61B 5/107*   (2006.01)
*G06T 7/00*    (2017.01)

(52) U.S. Cl.
CPC ............... *A43D 1/025* (2013.01); *A43D 1/08* (2013.01); *A61B 5/1074* (2013.01); *A61B 5/1079* (2013.01); *G06T 7/0012* (2013.01)

(58) Field of Classification Search
CPC ........ A43D 1/025; A43D 1/08; A61B 5/1074; A61B 5/1079; G06T 7/0012
See application file for complete search history.

(56) References Cited

U.S. PATENT DOCUMENTS

| | | | |
|---|---|---|---|
| 7,236,948 B1 | 6/2007 | Mochimaru | |
| 10,701,999 B1* | 7/2020 | Borenstein | G06Q 30/0623 |
| 2004/0081336 A1* | 4/2004 | Brooks | A43D 1/025 |
| | | | 33/515 |
| 2017/0068774 A1* | 3/2017 | Cluckers | A61B 5/743 |

FOREIGN PATENT DOCUMENTS

| | | | |
|---|---|---|---|
| DE | 29914186 U1 | 4/2000 | |
| DE | 102004029162 A1 | 1/2006 | |
| DE | 202012101055 U1 | 4/2012 | |
| DE | 202012006681 U1 | 9/2012 | |
| DE | 102012204537 A1 | 9/2013 | |
| EP | 2186429 A1 * | 5/2010 | A43B 7/147 |
| EP | 2186429 A1 | 5/2010 | |

(Continued)

*Primary Examiner* — Khai M Nguyen
(74) *Attorney, Agent, or Firm* — LUCAS & MERCANTI, LLP; Klaus P. Stoffel

(57) ABSTRACT

Custom-made shoes and orthopedic insoles support the wearer, with these products being manufactured at specialist retailers by a method that includes the steps of: producing a footprint; capturing the footprint and a measurement standard as a footprint image using a camera; and, extracting and/or determining the characteristic foot data on the basis of the footprint image.

14 Claims, 1 Drawing Sheet

(56) References Cited

FOREIGN PATENT DOCUMENTS

| EP | 2425734 | A1 | | 3/2012 | | |
|----|---------|-----|---|--------|---|---|
| EP | 2425734 | A1 | * | 3/2012 | ............ | A43D 1/022 |
| EP | 2586323 | A1 | | 5/2013 | | |
| JP | 2004219404 | A | | 8/2004 | | |
| JP | 2006141651 | A | | 6/2006 | | |
| JP | 4609640 | B2 | | 1/2011 | | |
| KR | 2014-0038890 | A | * | 9/2013 | | |
| KR | 20140038890 | A | * | 9/2013 | | |
| KR | 20140038890 | A | * | 3/2014 | | |
| WO | 0173688 | A2 | | 10/2001 | | |
| WO | 2014201498 | A1 | | 12/2014 | | |
| WO | WO-2017057388 | A1 | * | 4/2017 | | |

* cited by examiner

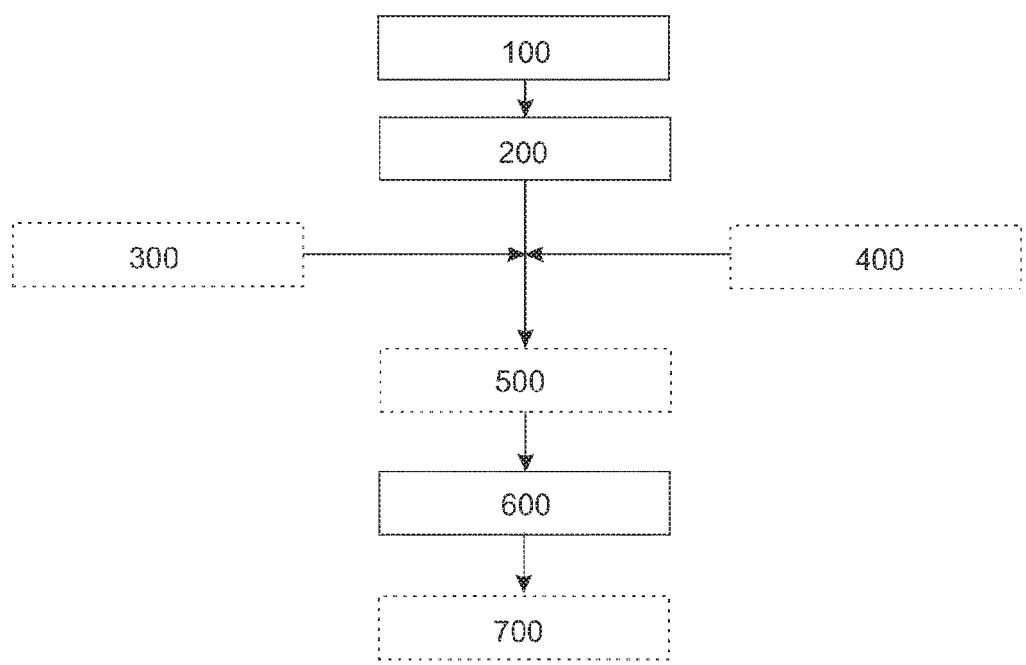

METHOD FOR DETERMINING CHARACTERISTIC FOOT DATA, COMPUTER PROGRAM AND APPARATUS

CROSS-REFERENCE TO RELATED APPLICATIONS

The present application is a 371 of International application PCT/EP2018/082758, filed Nov. 28, 2018, which claims priority of DE 10 2018 103 695.7, filed Feb. 20, 2018, the priority of these applications is hereby claimed and these applications are incorporated herein by reference.

BACKGROUND OF THE INVENTION

A method with a plurality of method steps is proposed for determining characteristic foot data for the manufacture of insoles and/or shoes, wherein a footprint is produced.

A human being typically covers a distance of over 100,000 kilometers in a lifetime. It is in this respect particularly important for the foot to be well, comfortably and healthily shod. Most shoes are offered for sale by retailers in standard sizes.

Bespoke shoes also exist, along with individual custom-made shoes, orthopedic custom-made shoes and/or orthopedic insoles. These serve to solidly and healthily support the foot.

To produce such custom-made shoes, orthopedic custom-made shoes or insoles, it is necessary to examine the feet individually. Such an examination generally takes place at specialist retailers, typically by measuring the feet using scanner devices or by measuring manually. It is in this case essential, however, to visit the respective specialist retailer. For the purpose of making such shoes or insoles, it is desirable to be able to avoid the trip to the retailer for the measuring process.

Document DE 10 2004 029 162 A1, which constitutes the closest prior art, describes a method for producing a manufacturing drawing for insoles and footbeds. The method comprises the steps of: selecting a foot type from a predetermined list; measuring defined foot dimensions; assigning a given set of individual fixed geometric elements as a function of the respective foot type according to a predetermined system; scaling the individual elements as a function of measured foot dimensions; and combining the individual elements for the purpose of manufacture according to a predetermined system.

SUMMARY OF THE INVENTION

According to the invention, a method is presented for determining characteristic foot data. The method is to be performed on a computer, computing device or a machine. The method can particularly preferably be executed as an application on a smartphone or tablet. The characteristic foot data in particular comprise shoe size, foot shape and/or foot dimensions. A person skilled in the art, for example an orthopedic shoemaker or an orthopedist, can use the characteristic foot data to produce the shoe, an insert or a sole which is individually adaptable and/or adapted to the person.

The method is in particular for performance for a user who desires the production of a shoe, an insole or a sole. The method is intended for performance at home or at any desired location. It is in particular not necessary to visit a specialist shop, for example an orthopedic retailer, to perform the method.

One method step provides that a footprint of the foot of the user is produced. In particular, the footprint constitutes an image or a partial image of the foot. The footprint is specifically an image, a partial image or an impression of the bottom of the foot. The impression in particular reproduces wholly or in part the heel, the outer edge of the foot, the longitudinal arch and/or the ball of the foot. In particular, the image and/or the footprint show the toes. The footprint in particular has an impression surface. The footprint is further distinguished by a footprint length and a footprint width. The footprint may be two- or three-dimensional. In particular, the footprint may have a depth of information, for example may use different colors or patterns.

In a further method step, a footprint image of the footprint and a measurement standard is captured using a camera. The camera is for example a color camera or a thermal imaging camera, or alternatively the camera is a black and white camera. The camera may in this case capture a single exposure as the footprint image, or alternatively a combined and/or multilayer image is captured as the footprint image. The camera is for example a digital camera and specifically the camera is the camera of a smartphone or tablet. It is particularly preferable for the image of the footprint to be captured with the camera in a perpendicular plan view onto the footprint. Alternatively, the footprint image may be captured by oblique capture of the footprint. The footprint image in this case in particular shows the entire footprint. The footprint may be captured with the camera at any desired distance or distance range. Furthermore, a measurement standard may be imaged and/or captured in the footprint image, with the footprint. The measurement standard in this case forms a scale. The measurement standard serves to enable true to scale evaluation of the footprint. The measurement standard may be a ruler or an additionally introduced portion or object. The measurement standard is in particular of two-dimensional configuration, wherein the measurement standard for example defines a Cartesian coordinate system.

In a further method step, the characteristic foot data are extracted and/or determined from the footprint image. In this case, for example, the footprint length and the footprint width are determined by means of the measurement standard. The footprint width and the footprint length are here specifically determined using a world coordinate system, i.e. the actual length and size, on the user. In particular, shoe size and/or foot shape is/are determined using the footprint image. The characteristic foot data may here be determined using image analysis algorithms and/or numerical methods. In particular, provision may be made for the characteristic foot data to be output to the user or a recipient, for example printed out or sent. The recipient may for example be a shoe or insole manufacturer, who for example receives the characteristic foot data by email or data transmission in an app.

The method may in particular also comprise the production of the shoe, wherein the shoe and/or the insole is/are produced on the basis of the characteristic foot data. In particular, the shoe and/or insole that has/have been produced is/are then compared with the characteristic foot data and/or the footprint image. The shoe and/or insole that has/have been produced may for example be superimposed with the footprint in the footprint image.

The consideration underlying the invention is that of providing a method which allows a user to have insoles or orthopedic shoes made without first having to visit the respective retailer for foot measurement. The method can be performed at home and characteristic foot data needed for production can be transmitted and provided to the user and/or the recipient, for example the specialist retailer. In particular, use of the measurement standard provides a reliable method which takes account in particular of distortion effects.

The insole and/or shoes may be produced by 3D milling, 3D printing, molding with a stripper plate and/or thermoforming methods. In particular, purchasing advice or a suggestion of suitable shoes and/or brands can be given on the basis of the characteristic foot data, wherein in particular the substructures of the footprint are taken into account here. In this case, for example, the characteristic foot data can or has to be compared with characteristic data relating to the shoes and/or brands. To this end, for example, the characteristic shoe and/or brand data are stored in a database. Through comparison with the stored characteristic data, the ideal shoe and/or the ideal brand can be determined.

The characteristic foot data preferably comprise a substructure of the footprint and/or of the foot. The substructure may for example include a pressure distribution on setting down and/or rolling the foot. The characteristic foot data for example form a map of the pressure distribution. In addition, the characteristic foot data may include information about inclinations. For example, the characteristic foot data include information about how the foot usually rolls, in particular whether the person sets down their foot on the heel or the toes. Specifically, the characteristic foot data include positions, quantities and/or information about calluses and/or corns.

In one configuration of the invention, the footprint takes the form of a 2D footprint. The 2D footprint may in particular be produced on a plate, for example an indicator plate, or paper. The footprint may for example be an impression which has arisen from normal walking on the ground. The 2D footprint in this case extends in the direction of the longitudinal arch and perpendicularly to the longitudinal arch. The 2D footprint may be produced on an arched or flat surface. In particular, the 2D footprint is an optical image of the bottom of the foot. The footprint, in particular the 2D footprint, contains information about the pressure distribution on production of the footprint.

It is particularly preferable for the footprint to be produced through previous wetting of the foot with a liquid. The liquid may be a colorless liquid or a colored liquid. In particular, the liquid may be bonded adhesively to the foot. The liquid may be oily and/or viscous. The liquid may comprise chemical additives, which have an indicator property on contact with a counterpart substance. Once the foot has been wetted with the liquid, it is placed onto a surface and for example rolled thereover. By setting the foot down onto the surface and/or rolling it thereover, some of the liquid will remain adhered to the surface and so form the footprint. The surface may be a standardized surface, for example in a DIN size, in particular DIN A4 or DIN A3. In particular, the surface may be formed of an indicator plate. Further examples of surfaces are a stone slab or a general floor covering. Rolling or setting down the foot on a textile, for example fabric, is likewise possible, wherein some of the liquid is then wiped off on this textile.

It is particularly preferable for the liquid for wetting the foot when producing the footprint to be water. In this case, the foot is dipped briefly into water, preferably allowed to drip for a short time, and then placed onto the surface. Some of the water is transferred to the surface, such that the water then wets the surface. In particular, the water may be detected as a reflection on the surface or the generation of a color change. For example, a textile becomes partially transparent when wetted with the water on production of the footprint, such that a color change is detectable. The consideration underlying this configuration is that of providing a method which can be performed at home and is not associated with any risks to the user, in particular of a health-related nature.

The footprint is optionally produced on a sheet of paper. The sheet of paper is in particular a standardized sheet of paper, for example DIN A1, DIN A2, DIN A3, DIN A4, DIN A5, or alternatively the sheet of paper may be of a US paper size or another paper size. The sheet of paper forms the measurement standard when capturing the footprint image. Since the dimensions of the sheet of paper of the corresponding paper size are known, said sheet can be used as a scale and unit of measure. If the method can be performed on a computing device, a smartphone or another electronic unit, the paper size may in particular be set, such that the method is carried out with the correct scale and/or the correct measurement standard. Provision may moreover be made for the country of application to be predetermined and the appropriate paper size selected on the basis thereof, for example if the country is set as the USA, then US paper sizes are used, and in particular it is also identified on the basis of the ratio of paper to foot which precise size it must be.

For example, a foot appears larger on a sheet of DIN A4 paper than on a sheet of DIN A3 paper. The consideration underlying this configuration is that of configuring the method such that the measurement standard and/or the scale can be achieved with everyday means.

In particular, the footprint image is captured with a first device. The first device is for example a smartphone, a tablet or a digital camera. The first device preferably has an interface for data exchange, wherein the interface is for example a radio interface, in particular a WiFi interface. The characteristic foot data are determined from the footprint image on a second device. The second device may for example be a central device, for example a central server, which may be reached via an internet or other data link. The footprint image is forwarded from the first device to the second device. For example, the footprint image is forwarded from the first device to the second device over an internet connection, a WiFi connection, an infrared connection, a Bluetooth connection or over a cable connection.

Furthermore, further data may be transferred from the first and second device via the connection, for example an additional image, an additional video and/or additional data. It is moreover possible for the characteristic foot data which have been determined by the second device to be sent to the first device and/or provided to the first device. The consideration underlying this configuration is that of locating the intelligence of the method centrally, for example on a server, and outsourcing the measures for providing the footprint image to a first device in a data-saving manner, wherein the first device may be used at home.

It is particularly preferable for a point of interest on the foot to be marked with a marker prior to production of the footprint and/or prior to wetting of the foot with the liquid. The point of interest may for example be a pain point, a contact point or a problem point. In particular, multiple points of interest may be marked with the marker. Provision may further be made for the points of interest of different types, for example pain point and contact point, to be marked with different markers. The marker is for example a pencil, a paste or a further liquid. In particular, the marker is a colored pencil and preferably a lipstick. The marker may also comprise a fluorescent marker or a hydrophobic component, to which water does not adhere. On transfer and/or production of the footprint, for example on the sheet of paper, the marker is transferred to the latter. The marker shows the precise position of the points of interest on the footprint. In particular, the marker is imaged in the footprint image. On the basis of the marker in the footprint image, the point of interest may be taken into account when manufacturing the insole and/or the shoe. The consideration underlying this configuration is that of providing a method which also takes account of problem points and/or points of interest, wherein they may be taken into account using simple means.

Provision is optionally made for an additional image and/or additional video of the foot to be captured using the camera. The additional image and/or the additional video may show a side view, an oblique view or any desired view of the foot. In particular, provision may be made for the additional image to image the foot span and/or a calf or lower leg. The characteristic foot data are determined on the basis of the additional image together with the footprint image. The additional image combined with the footprint image makes it possible, for example, to integrate a proportional impression with regard to tissue condition into manufacture and/or determination of the characteristic foot data. Furthermore, conclusions may be drawn as to fleshiness, shoe size or misalignments, wherein these may be included in the characteristic foot data.

It is particularly preferable for the additional image to show a plan view onto the foot. In particular, it is a plan view perpendicular to the foot and/or perpendicular to the bottom of the foot. The plan view preferably shows the back of the foot.

It is particularly preferable for additional data to be collected. The additional data are for example integrated into the first device or may be provided thereto. Using the additional data, it is possible, together with the footprint image and/or the additional image, to determine the characteristic foot data. In particular, the characteristic foot data may be refined and/or supplemented with the additional data. Specifically, provision may be made for the additional data to be provided to the second device.

The additional data for example include the age of the user, the weight of the user, the gender of the user, the height of the user, an already known shoe size of the user, the heel size of the user or the ball size of the user. Furthermore, angular positions of the legs may be taken into account as an additional dimension. The additional data specifically include details of diseases such as for example diabetes or polyneuropathies, clinical syndromes, injuries, such as for example deformation, amputations, inflammation, previous fractures and/or sprains. Furthermore, the additional data may comprise information about footwear and/or preferred types of sport, in order for example to determine insole type and/or shape and thickness of the insole.

On the basis of the additional data, the characteristic foot data may include loading, loading points, weight distribution and/or information relating to insole softness.

Specifically, provision may be made for the additional data to include a gait analysis, length of pace, a step count, number of stories and/or a pelvis rotation. The pelvis rotation and/or the length of pace may for example be measured using a gyroscope, wherein the gyroscope is for example fitted to the pelvis and/or in the user's pants pocket. The gyroscope is for example part of a cell phone, smartphone, tablet and/or the first device. The daily step count, stories climbed, for example per day, or length of pace may in particular be determined by means of a fitness tracker and/or pedometer, wherein for example the data from the fitness tracker and/or from the pedometer may for example be transferred by means of a tracker interface, wherein the tracker interface is arranged on the first or second device.

It is particularly preferable for the characteristic foot data to include information about misalignments. For example, the characteristic foot data include information about foot type, for example whether the foot is a splayfoot, a rigid flatfoot, a supple flatfoot, exhibits pes valgus and/or is a club foot. The characteristic foot data may also include pain points. The consideration underlying this configuration is that of providing a method which may determine all essential and necessary information and/or characteristic foot data for producing the insole and/or the shoe.

A computer program for performing the method is a further subject of the invention. The computer software is configured in particular for execution on a computing unit, a computer or a mobile device. The mobile device is for example a cell phone, a tablet or a smartphone. If the computer program is executed on the mobile device, the computing unit or the computer, all the steps of the method are performed. The computer program is in particular an app for a smartphone. Specifically, the computer program is intended for use on the first device. Furthermore, the computer program may be stored in part on the first device and the second device, wherein these two parts of the computer software together execute the method as a whole.

The invention further provides an apparatus for executing the computer program and/or for performing the method. The apparatus is preferably a smartphone or a tablet. By means of the apparatus it is possible to capture the footprint, wherein the apparatus further comprises a computing unit and/or a processor unit by means of which the characteristic foot data may be determined from the captured footprint, in particular the footprint image. The apparatus preferably comprises the camera.

BRIEF DESCRIPTION OF THE DRAWING

Further advantages, features and/or effects of the invention are revealed by the appended figures and the description thereof. In the figures:

FIG. 1 shows a flowchart of the method for determining characteristic foot data.

DETAILED DESCRIPTION OF THE INVENTION

FIG. 1 is a schematic representation of a flowchart for determining characteristic foot data using the method. In a first method step 100, the footprint is produced. In the process, the foot of the user who wishes for the insole and/or shoe to be manufactured is wetted with a liquid. In particular, the foot is wetted with water. Furthermore, provision may be made for points of interest to be marked with a marker, in particular with a lipstick, prior to wetting with the liquid. Points of interest are for example pain points or pressure points in previous shoes.

After wetting and marking of points of interest, the foot is set down on and/or rolled over a surface. The surface is for example formed of an indicator plate, but preferably the surface is formed of a sheet of paper. The sheet of paper is in this case in particular a standard sheet of paper, as is conventionally used in the office and/or everyday life. In particular, the sheet of paper is a DIN A4 or a DIN A3 sheet. The sheet of paper is particularly preferably a sheet of absorbent paper, for example a filter paper.

The method provides a second method step 200. Method step 200 is production of a photo of the footprint together with a measurement standard. Method step 200 is applied in particular before the liquid has dried on the sheet of paper. The photo is captured with a camera, in particular a smartphone or tablet camera. The photo of the footprint 20 with the measurement standard forms a footprint image. The footprint image is a two-dimensional image of the footprint. The footprint image shows the structures, for example toes, ball of the foot and heel of the footprint. From the footprint image, it is in particular possible to determine pressure distributions on production of the footprint and/or areas and lengths of the footprint. In particular, provision may be made for the footprint image to be a black and white or grayscale image for the purpose of reducing data volume. The footprint image is particularly preferably generated in a perpendicular plan view onto the footprint and/or the sheet of paper. Alternatively, the footprint image may be generated in an oblique view onto the sheet of paper and/or the footprint.

The footprint image comprises a measurement standard. The measurement standard forms a scale with the assistance of which the footprint may be measured. To this end, the measurement standard comprises one length scale in two linearly independent directions and/or length scales in two independent directions may be determined from the measurement standard. The measurement standard may be a ruler or a reference object, for example a check guarantee card or another object. Particularly preferably, however, the measurement standard is formed of the sheet of paper. Since the sheet of paper is a standardized sheet of paper, for example DIN A4 paper, the footprint may be measured on the basis of the outer edges, the lengths of which are known.

A method step 300 is optionally provided, in which an additional image or an additional video is provided. The additional image for example shows the foot in plan view, for example the back of the foot, and/or a side view. In addition, the additional image may be an image from behind of the legs and feet, such that angles may be determined from leg position. The additional image in the plan view from above, which shows the back of the foot, may be used for example to determine the fleshiness of the foot and/or its condition, for example tissue condition.

Moreover, an optional method step 400 may be provided, in which additional data are provided and/or input. The additional data for example include the age, gender, weight and height of the user, details of diseases, injuries and/or details of preferred types of sport or shoe brands. These additional data may for example be input by means of an input device and/or a data form. The additional data may be used for example to determine the pressure distribution of a footprint in greater detail and/or to define typical foot shapes, which are dependent on gender.

Optionally, a method step 500 is further provided, in which data from a first device are transferred to a second device. The first device is for example a tablet or a smartphone. The first device is configured to capture the footprint image, the additional image, additional videos and/or the additional data. Method steps 100, 200, 300 and 400 are performed, for example on an app of the smartphone. In method step 500, the footprint image, the additional image, the additional video and/or the additional data are transmitted and/or sent from the first device to the second device. This transmission and/or sending may proceed for example via an internet connection, a radio link or a cable connection. The second device is in this case for example a central server or a computing unit. The second device may be operated by a manufacturer of the insoles and/or shoes.

In method step 600, characteristic foot data are determined. The characteristic foot data 600 are determined from the footprint image. In addition, the addition image, the additional video and/or the additional data are used to determine the characteristic foot data. The characteristic foot data for example comprise shoe size, foot length and/or foot width, a foot type, for example splayfoot, flatfoot or clawfoot, and/or weight distribution when walking. The characteristic foot data may also include an axial misalignment or the necessary insole softness. The characteristic foot data in particular form a collection of data, on the basis of which the insole and/or the shoes may be manufactured, wherein this data set in particular forms a complete data set which requires no supplementation.

A method step 700 is optionally provided, wherein in method step 700 the characteristic foot data are transmitted from the second device to the first device, such that the user receives information about the data obtained and/or optionally may put this to further use. Provision may further be made for the second device to transmit the characteristic foot data to a factory or production shop, such that the shoes or insoles may be quickly and reliably manufactured. Sending the characteristic foot data to the factory and/or production shop may require prior approval or confirmation by the user. The characteristic foot data may furthermore be forwarded to paying authorities such as for example health insurance companies, in order in particular to be approved and/or a to enable transmission of a cost estimate.

The invention claimed is:

1. A method for determining characteristic foot data for the manufacture of insoles and/or shoes, having the method steps of:
   producing a footprint on a standardized sheet of paper that is an impression left by a bottom of the foot on the standardized sheet of paper, wherein dimensions of the standardized sheet of paper are known;
   capturing the footprint and a measurement standard as a footprint image using a camera, the standardized sheet of paper forming the measurement standard; and
   extracting and/or determining the characteristic foot data on the basis of the footprint image and the measurement standard by using the standardized sheet of paper as a scale and unit of measure.

2. The method according to claim 1, wherein the characteristic foot data comprise a substructure of the footprint and/or of the foot.

3. The method according to claim 1, wherein the footprint takes the form of a 2D footprint.

4. The method according to claim 1, wherein the footprint is produced by wetting the foot with a liquid and subsequently rolling it over a surface.

5. The method according to claim 4, wherein the liquid is water.

6. The method according to claim 1, wherein the footprint image is captured using a first device, wherein the footprint image is sent by the first device to a second device for determining the characteristic foot data.

7. The method according to claim 1, wherein, prior to production of the footprint, points of interest on the foot are marked with a marker, in particular a lipstick, wherein the marker indicates the points of interest in the footprint.

8. The method according to claim 1, wherein an additional image of the foot is captured, wherein the characteristic foot data are determined on the basis of the additional image and the footprint image.

9. The method according to claim 1, wherein the additional image shows a plan view onto the foot.

10. The method according to claim 1, wherein additional data are collected, wherein the additional data are included in the determination of the characteristic foot data.

11. The method according to claim 10, wherein the additional data comprise the age, weight, height, shoe size and/or gender of a user.

12. An apparatus for performing the method according to claim 1, wherein the apparatus comprises a camera.

13. A computer program product for determining characteristic foot data, wherein, when the computer program product is configured to be executed on a computing unit, a mobile device and/or an apparatus, wherein the computer program product is configured to determine characteristic foot data based on an image of a footprint captured using a camera, wherein the footprint is an impression left by a bottom of the foot on a standardized sheet of paper of known dimensions, wherein, on execution of the computer program product, a method is carried out that includes the steps of:
- producing the footprint that is the impression left by the bottom of the foot on the standardized sheet of paper,
- capturing the footprint and a measurement standard as a footprint image using the camera, the standardized sheet of paper forming the measurement standard,
- extracting and/or determining the characteristic foot data on the basis of the footprint image and the measurement standard by using the standardized sheet of paper as a scale and unit of measure.

14. An apparatus for executing the computer program product according to claim 13, wherein the apparatus comprises a camera.

* * * * *